(12) United States Patent
Zeng et al.

(10) Patent No.: US 10,537,427 B2
(45) Date of Patent: Jan. 21, 2020

(54) VALVE STENT USED SAFELY AND VALVE REPLACEMENT DEVICE HAVING THE SAME

(71) Applicant: VENUS MEDTECH (HANGZHOU), INC., Hangzhou, Zhejiang (CN)

(72) Inventors: Frank Zeng, Hangzhou (CN); Larry Lo, Hangzhou (CN); Jess Qi, Hangzhou (CN)

(73) Assignee: Venus Medtech (Hangzhou) Inc., Hangzhou (CN)

( * ) Notice: Subject to any disclaimer, the term of this patent is extended or adjusted under 35 U.S.C. 154(b) by 0 days.

(21) Appl. No.: 15/715,961

(22) Filed: Sep. 26, 2017

(65) Prior Publication Data

US 2018/0049871 A1 Feb. 22, 2018

Related U.S. Application Data

(63) Continuation-in-part of application No. PCT/CN2015/078944, filed on May 14, 2015.

(30) Foreign Application Priority Data

Mar. 26, 2015 (CN) .......................... 2015 1 0136304

(51) Int. Cl.
*A61F 2/24* (2006.01)

(52) U.S. Cl.
CPC .... *A61F 2/2418* (2013.01); *A61F 2210/0014* (2013.01); *A61F 2230/0078* (2013.01); *A61F 2250/0026* (2013.01)

(58) Field of Classification Search
None
See application file for complete search history.

(56) References Cited

U.S. PATENT DOCUMENTS

| 2010/0082094 A1* | 4/2010 | Quadri ................. A61F 2/2412 |
| | | 623/1.26 |
| 2010/0094411 A1 | 4/2010 | Tuval et al. |
| 2010/0268332 A1 | 10/2010 | Tuval et al. |

(Continued)

FOREIGN PATENT DOCUMENTS

| CN | 102113921 A | 7/2011 |
| WO | WO2014/127750 | 8/2014 |
| WO | WO2015/065646 | 5/2015 |

OTHER PUBLICATIONS

Supplementary European Search Report dated Sep. 21, 2018 for corresponding European Application No. EP 15 88 5936.

(Continued)

*Primary Examiner* — Leslie Lopez
(74) *Attorney, Agent, or Firm* — Raymond Sun

(57) ABSTRACT

The present invention provides a valve stent used safely comprising a supporting net frame, and a flared section connected to an end of the supporting net frame; wherein the flared section is connected to all end nodes located at a corresponding side of the supporting net frame, the flared section is grid shaped, and a number of intersection points of the grids decreases along an axial direction away from the supporting net frame. The present invention also provides a valve replacement device comprising an above valve stent and a prosthesis valve fixed inside the supporting net frame.

19 Claims, 5 Drawing Sheets

(56) References Cited

U.S. PATENT DOCUMENTS

2011/0264196 A1* 10/2011 Savage ................ A61F 2/2418
623/1.26
2011/0319988 A1* 12/2011 Schankereli .......... A61F 2/2418
623/2.11
2013/0282113 A1* 10/2013 Punga ................... A61F 2/2418
623/2.17

OTHER PUBLICATIONS

Office Action and search report dated Dec. 17, 2018 for corresponding Russian Application No. 2017137520/14.

* cited by examiner

VALVE STENT USED SAFELY AND VALVE REPLACEMENT DEVICE HAVING THE SAME

CROSS-REFERENCE TO RELATED APPLICATIONS

This application is a continuation-in-part of International Application No. PCT/CN2015/078944, filed May 14, 2015, which claims the benefit of Chinese Application No. 201510136304.5, filed Mar. 26, 2015 in the State Intellectual Property Office. All disclosures of the documents named above are incorporated herein in their entirety by reference.

FIELD OF THE INVENTION

The present invention relates to the technical field of medical apparatuses, and in particularly to a valve stent used safely and a valve replacement device having the same.

BACKGROUND

In the prior art, an interventional cardiac valve generally includes a compressible valve stent and a plurality of leaflets, wherein the valve stent has good biological compatibility, and can be positioned at a corresponding cardiac valve location safely, stably, and reliably.

A main body of a valve stent is usually a rhombic unit structure, which is configured to meet the requirement of compressibility. However, the rhombic unit structure may form independent rhombic vertices, and these rhombic vertices existing in isolation are usually sharp. During the use process of the valve stent, there is a risk that the rhombic vertices existing in isolation pierce a sheath.

If the rhombic vertices existing in isolation are gathered at an end portion of the valve stent, the risk of piercing is relatively low. However, in order to be fit for particular structures of different valves of hearts, valve stents used in different positions have different structures.

Taking a pulmonary valve as an example, in order to make the location of the valve at the main pulmonary artery more stable, the valve stent is further provided with a flared section located at a branch location of the main pulmonary artery, that is, the rhombic units structure at the end portion of the valve stent are extended further in an axial direction of the valve stent and expanded in a radial direction of the valve stent, such that this portion is softer and can resiliently match with a blood vessel wall, thereby preventing the blood vessel wall from being stabbed or even pierced. However, the changes of the structure on the end portion may cause some vertices of the rhombic unit structures of the valve stent, which exist in isolation, to be exposed.

For example, a Chinese patent application publication CN102961199A discloses a pulmonary artery valve stent which can prevent displacements. The pulmonary artery valve stent includes a valve suture section, an artificial valve connected with the valve suture section, and a position limiting structure connected with a distal end of the valve suture section. The valve suture section is located in a right ventricular outflow tract or a main body of the pulmonary artery after being released, and a vertex portion of the position limiting structure abuts against an intersecting portion of the main body of the pulmonary artery and a branch of the pulmonary artery after being released, thereby providing an axial limiting function. In this patent document, the valve suture section is formed by a plurality of rhombic structure units; when the distal end of the valve suture section is connected with the position limiting structure, some rhombic vertices of the rhombic structure existing in isolation may remain, and these rhombic vertices existing in isolation are potential safety hazards during the use process.

For another example, a Chinese patent CN101951858B discloses a funnel shaped throttling device. As shown in FIG. 1, the funnel shaped throttling device includes a middle portion having rhombic grid structures, and two end portions of flared shape connected to two ends of the middle portion respectively. The middle rhombic grid structures has a plurality of rhombic vertices 10 existing in isolation, may cause much inconvenience during operation process.

When a valve stent is compressed inwards a sheath pipe, the rhombic vertices existing in isolation will become spines. The spines are prone to stab the sheath pipe when passing through complex and curved anatomic paths in a human body. In the subsequent process of releasing valve, they may also result in too much resistance and pierce the sheath pipe, and thereby cause the valve to be unable to release successfully; in extreme cases, they may stab or even pierce blood vessel walls, and then cause great harm to patients.

SUMMARY OF THE INVENTION

In view of the above problems, it is necessary to provide a valve stent used safely and a valve replacement device with the valve stent, which eliminates rhombic vertices existing in isolation which are present in non-end portions of the valve stent, preventing spines from appearing after the valve stent is compressed while maintaining the mechanical properties of the original structural, and thereby resolving the problem of sheath damaged caused by the spines.

The proximal end and the distal end referred in the present invention are relative, specifically, the end away from the operator during the operation is the distal end, and the end adjacent to the operator is the proximal end.

A valve stent used safely comprises a supporting net frame and a flared section connected to an end of the supporting net frame, the flared section is connected to all end nodes located at a corresponding side of the supporting net frame, the flared section is grid shaped, and a number of intersection points of the grids decreases along an axial direction away from the supporting net frame.

In certain embodiments, the flared section is located at a precedent release end of the valve stent.

In certain embodiments, an outer rim of the flared section is formed by a plurality of curved supporting bars, and the end nodes of the supporting net frame corresponding to the positions of the supporting bars are all connected to the supporting bars.

In certain embodiments, the end nodes intersect the supporting bars, or are connected with the supporting bars tangentially and intersectingly by guiding bars.

In certain embodiments, wherein each of the guiding bars is curved and has at least one inflection point.

In certain embodiments, each guiding bar is formed by two arc sections and the at least one inflection comprises a first inflection point.

In certain embodiments, a connecting line from a proximal end of each guiding bar to the first inflection point gradually deviates away from the supporting net frame along an extension direction.

In certain embodiments, an included angle of the connecting line connecting the proximal end of the guiding bar and the first inflection point and an axis of the supporting net frame is in the range of 30° to 90°.

In certain embodiments, an included angle of the connecting line connecting the proximal end of the guiding bar and the first inflection point and an axis of the supporting net frame is ranged between 45° to 60°.

In certain embodiments, a connecting line connecting a distal end of each guiding bar and a corresponding inflection point extends gradually towards the supporting net frame.

In certain embodiments, the connecting line connecting the proximal end of the guiding bar and the inflection point is the first connecting line, and the connecting line connecting the distal end of the guiding bar and the inflection point is the second connecting line, an included angle of the first connecting line and the second connecting line is ranged between 90° and 180°.

In certain embodiments, the included angle of the first connecting line and the second connecting line is ranged between 100~150°.

In certain embodiments, an acute angle is formed between each guiding bar and a corresponding supporting bar.

In certain embodiments, the acute angle formed between each guiding bar and a corresponding supporting bar is in the range of 10° to 60°.

In certain embodiments, each supporting bar comprises two first bar bodies and a second bar body connecting distal ends of the two first bar bodies, and a proximal end of each first bar body is connected to a corresponding end node.

In certain embodiments, the first bar body deviates gradually away from the supporting net frame along an extension direction from the corresponding end node to the second bar body, and the second bar body extends towards the supporting net frame from the intersection point with the first bar body.

In certain embodiments, an included angle between a line connecting two ends of each first bar body and the axis of the supporting net frame is in the range of 30° to 60°.

In certain embodiments, the supporting net frame comprises a blood inlet to allow blood flowing in and a blood outlet opposite to the blood inlet, the flared section is located at the blood outlet end of the supporting net frame.

In certain embodiments, a ratio of an axial length of the transition section before being compressed to an axial length of the transition section after being compressed is 1.

In another aspect, a valve stent used safely is provided, which comprises a supporting net frame, and a flared section connected to an end of the supporting net frame, wherein the flared section comprises an outer flared segment and an inner flared segment, the outer flared segment is connected with all the end nodes of the supporting net frame at the corresponding side by the inner flared segment.

In certain embodiments, the flared section is located at the precedent release end of the valve stent.

In certain embodiments, the outer flared segment comprises a plurality of outer flared segment units, and the inner flared segment comprises a plurality of inner flared segment units, each of the outer flared segment units and the inner flared segment units comprises two proximal ends and a distal end, the two proximal ends of each inner flared segment unit are connected to two corresponding end nodes of the supporting net frame, each pair of two adjacent inner flared segment units corresponds to an outer flared segment unit, and two distal ends the inner flared segment units of a pair of two adjacent inner flared segment units are connected to two proximal ends of a corresponding outer flared segment unit respectively.

In certain embodiments, each outer flared segment unit is formed by a curved first strut, and each inner flared segment unit is formed by two curved second struts intersecting each other, the first strut extends from two distal ends of two second struts which are located at an outside of a pair of inner flared segment units.

In certain embodiments, among each pair of inner flared segment units, the two second struts located at the inner side are defined as inner struts, and the two second strut located at the outer side are defined as outer struts, each inner strut has an inflection point.

In certain embodiments, each inner strut is formed by two arc sections, and the at least one inflection comprises a first inflection point at an intersection of the two arc sections.

In certain embodiments, a connecting line between a proximal end of the inner strut and the first inflection point deviates gradually away from the supporting net frame.

In certain embodiments, an included angle between the connecting line between the proximal end of the inner strut and the first inflection point and an axis of the supporting net frame is in the range of 30° to 90°.

In certain embodiments, the included angle between the connecting line between the proximal end of the inner strut and the first inflection point and an axis of the supporting net frame is in the range of 45° to 60°.

In certain embodiments, a connecting line connecting a distal end of each inner strut and a corresponding inflection point extends gradually towards the supporting net frame.

In certain embodiments, the connecting line connecting the proximal end of the inner strut and the inflection point is the first connecting line, and the connecting line connecting the distal end of the inner strut and the inflection point is the second connecting line, an included angle of the first connecting line and the second connecting line is ranged between 90° and 180°.

In certain embodiments, the included angle of the first connecting line and the second connecting line is ranged between 100°~150°.

In certain embodiments, each outer strut deviates gradually away from the supporting net frame from a corresponding end node towards a corresponding first strut.

In certain embodiments, an included angle between a line connecting two ends of each outer strut and the axis of the supporting net frame is in the range of 30° to 60°.

In certain embodiments, in an inner flared segment unit, an acute included angle is formed between the two second struts.

In certain embodiments, the acute included angle formed between the two second struts is in the range of 10° to 60°.

In certain embodiments, the inner flared segment gradually deviates away along an extension direction from the supporting net frame from the corresponding end nodes of the supporting net frame to the outer flared segment, and the outer flared segment gradually extends towards the supporting net frame. the inner flared segment gradually deviates away along an extension direction from the supporting net frame from the corresponding end nodes of the supporting net frame to the outer flared segment, and the outer flared segment gradually extends towards the supporting net frame.

In certain embodiments, an obtuse angle is formed between the inner flared segment and the outer flared segment.

The present invention further provides a valve replacement device, which includes the aforementioned valve stent and a prosthesis valve fixed inside the supporting net frame.

Further, the valve stent is a pulmonary valve stent. The stent can be formed by cutting a nickel-titanium alloy tube. The present invention utilizes a valve stent used safely and a valve replacement device which made modifications on conventional memory alloy self-expanding valve stent, eliminating the vertices existing in isolation and present at non-end portions of the valve stents, preventing spines from appearing after the valve stent is compressed while maintaining the mechanical properties of the original structural, and thereby resolving the problem of sheath damage caused by the spines. The technical solution of the invention is easy to implement and has no impact on the existing production process and the production efficiency. Only the modified drawing needs to be adopted in the laser cutting process of the valve stent without increasing the cost, the existing processing technology and molds can be used in subsequent process, the cost for product modification is low.

DETAILED DESCRIPTION OF THE PREFERRED EMBODIMENT

In order to make the object, the technical solution and the advantages of the present invention more apparent, the present invention is described in further detail in conjunction with the accompanying drawings. It should noted that the described embodiments is made for the purpose of merely illustrating the present invention, but not intended to make any limitation.

In the following, the valve stent according to the embodiments are illustrated, taking a pulmonary artery stent as an example.

Figure 1:
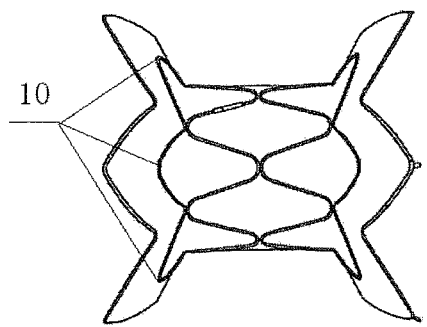
FIG. 1 is a schematic view of a valve stent in the prior art.
Figure 2:
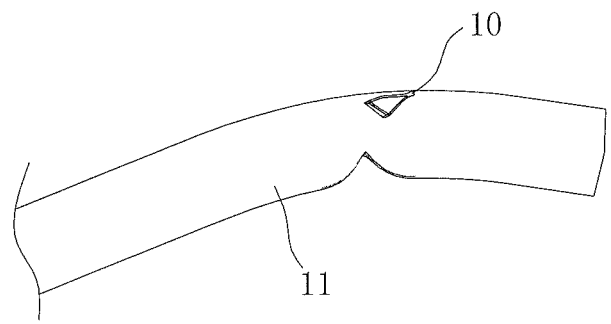
FIG. 2 is a schematic view showing that an isolated end node pierces a sheath, according to the prior art.

The pulmonary artery stent according in the prior art includes an inflow section for blood flowing in and an outflow section for blood flowing out, wherein there are end nodes existing in isolation at the outflow section. For example, end nodes 10 existing in isolation are formed in the outflow section as shown in FIG. 1. The end nodes 10 are not located at the distal end of the pulmonary artery stent. After the pulmonary artery stent is compressed into a sheath, the sheath is to be delivered to the lesion site of the patient along the blood vessel. As the outflow section of the stent is to be released precedently and the inflow section is to be released posteriorly, along the advancing direction of the sheath, in particular when the sheath passes through the curving vessel, the isolated end nodes 10 are prone to be deformed into spines and pierce the sheath 11, as shown in FIG. 2.

Once the end nodes become the spines and pierce the sheath, on the one hand, a potential risk of piercing the blood vessel wall or the heart will raise, casing damages to the patient; on the other hand, the stent is unable to expand successfully even though it reaches the implant site, at that moment, the only way to solve the problem is to retract the sheath, which may pierce the blood vessel wall, the heart ventricle and the heart atrium, and cause more serious damage to the patient.

Embodiment I

Figure 3:
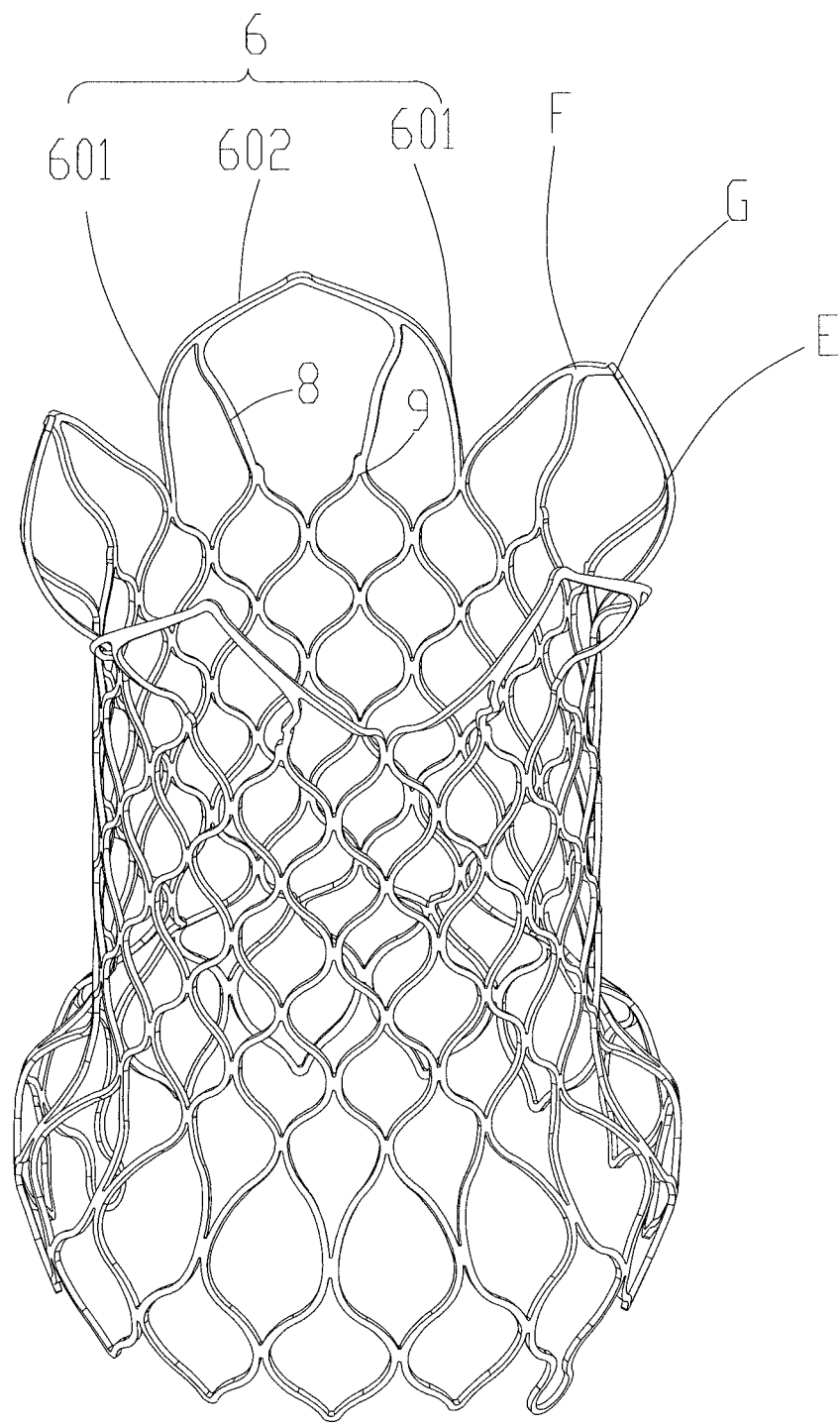
FIG. 3 is a perspective view of the valve stent used safely of the present invention.
Figure 4:
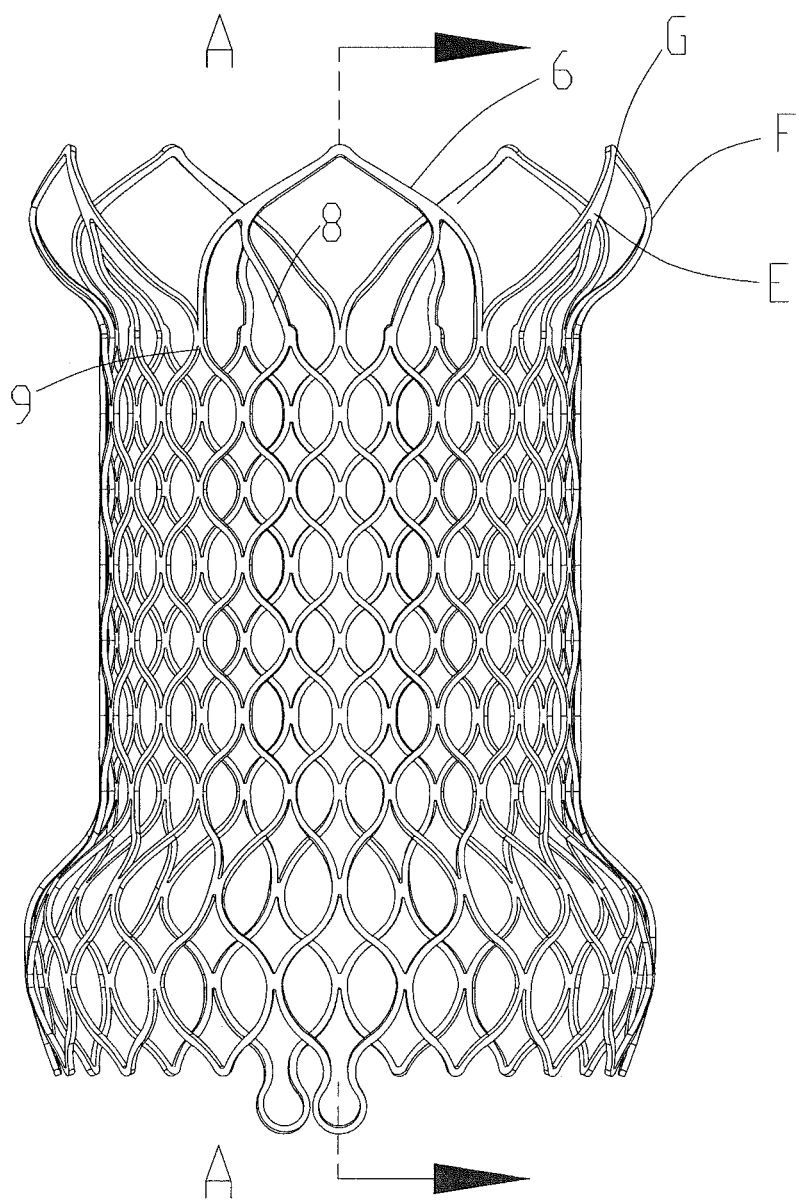
FIG. 4 is a front structural schematic view of the valve stent used safely of the present invention.

As shown in FIG. 3 and FIG. 4, the present invention provides a pulmonary artery stent which can be used safely, including a supporting net frame 12, and a flared portion connected at an end portion of the supporting net frame 12. The flared portion is connected to all the end nodes 9 at an adjacent end of the supporting net frame 12. The flared portion is in the form of a grid structure, and the number of intersection points of the grids decreases along an axial direction away from the supporting net frame 12.

It should be noted that, the term "intersection point" refers to the intersection where two adjacent grids intersect or connect, i.e., the node shared by adjacent grids. For example, point E and F shown in FIG. 3 are intersection points. The intersection points of the flared portion at an outermost side are idle. For example, the point G as shown, is formed by intersection of two lines of the grids, in particular, two curved line intersecting smoothly. The intersection portion at the intersection point G is a sharp corner which can facilitate the compressing of the stent.

The supporting net stent 12 refers to the part of the valve stent which serves to support the prosthetic valve, and is generally tubular shaped, to allow blood flowing inside the tube interacts with prosthetic valve. The supporting net stent 12 is not limit to the cylindrical shape having a constant diameter along an extension direction, but it is possible to have an end expanded or shrunken in a radial direction. The supporting net frame 12 has a plurality of rhombic units. All the end nodes 9 of the supporting net frame 12, namely the vertexes of the rhombic units adjacent to the flared portion, is connected to the flared portion, to avoid isolating vertexes appearing at the non-end portion of the valve stent, to avoid spine after the valve stent is compressed.

In this embodiment, there are two flared portions, which are respectively in the form of inflow section 5 and outflow section 1 respectively connected to two ends of the supporting net frame 12. The inflow section 5 and the outflow section 1 are identified depends on the flowing direction of blood. In an axial direction of the supporting net frame 12, the supporting net frame 12 includes a blood inlet and a blood outlet opposite to the blood inlet. The inflow section 5 is connected to the supporting net frame 12 at the blood inlet end to allow the blood flowing into the valve stent via the inflow section 5. The outflow section 1 is connected to the supporting net frame 12 at the blood outlet end, to allow the blood flowing out of the valve stent via the outflow section 1. Namely, blood flows into the valve stent via the inflow section 5, passes through the supporting net frame 12, and exits the valve stent from the outflow section 1. It is understood that, in alternative embodiments, the valve stent may have only one flared portion which is arranged at the precedent release end. It should noted that, the precedent release end of the valve stent is the end which is to be released precedently. The flared portion is arranged at the precedent release end can avoid spine which may pierces the sheath during advancing and/or retracting of the sheath. Even if spines are formed at a posterior release end of the valve stent, as the orientations of the spines are similar to the retracting direction of the sheath pipe, and thus the risk to cause the phenomenon that the spines pierce the sheath is very low. Therefore, preferably, the flared portion is necessarily arranged at the precedent release end. Typically, the blood outlet end of the supporting net frame is the precedent release end, and therefore, in the case of only one flared portion, the flared portion is connected to the supporting net frame 12 at the blood outlet end, that is, the flared portion is the outflow section connected to the supporting net frame 12 at the blood outlet end, as specifically shown in FIG. 5.

In the following, the structure of the flared portion will be described in detail by means of illustrating the outflow section 1.

Figure 5:
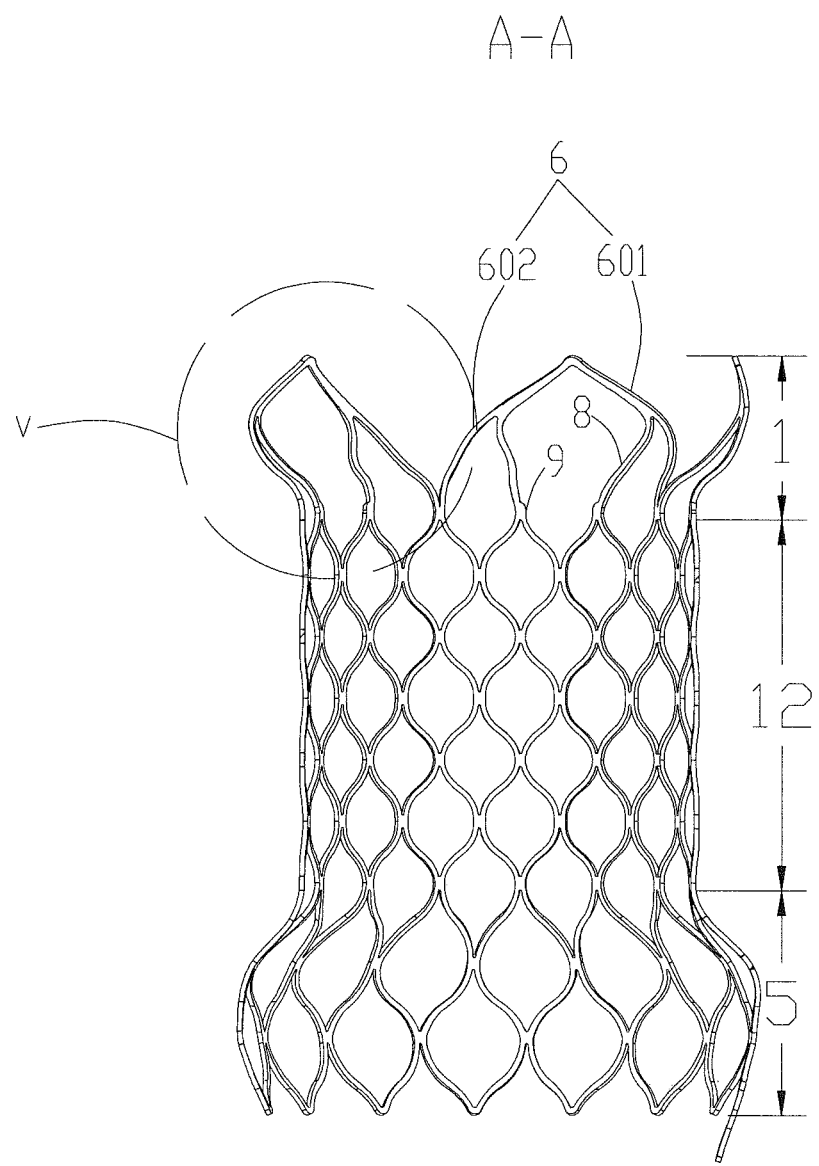
FIG. 5 is the sectional view of the valve stent of FIG. 4, along a line A-A.

Referring to FIGS. 3 to 5, the outflow portion 1 expand radially outwardly to form flared sections. An Outer rims of the outflow portion 1 is formed by a plurality of curved supporting bars 6. All the end nodes 9 of the supporting net frame 12 corresponding to the supporting bars 6 are connected to the supporting bars 6. The end nodes intersect the supporting bars 6, or are connected with the supporting bars 6 tangentially and intersectingly by guiding bars 8, with the guiding bars 8 nonintersecting each other. The grid units of the outflow section 1 is formed by the supporting bars 6 and the guiding bars 8 intersecting each other.

In this embodiment, each supporting bar 6 corresponds to four adjacent end nodes 9, and the four adjacent end nodes are assigned as one group of end nodes 9. In each group of the end nodes 9, two end nodes which are located at two ends are connected to the supporting bar 6 directly, and the other two end nodes 9 are connected with the supporting bar 6 tangentially and intersectingly by two guiding bars 8 with the two guiding bars 8 nonintersecting each other. Each guiding bar 8 and the supporting bar 8 intersect substantially at a middle portion of the outflow section 1 along the axial direction of the outflow section 1.

Each two adjacent groups of end nodes share a common end node 9. It is understood that, the common end node 9 is the one that is located at the end among the group. The common end node 9 is connected to two supporting bars 6 both, to connected the supporting bars 6 as well as the guiding bars 8 together as an integrated structure. As such, the number of intersection points of the grids of the outflow section 1 decreases along an axial direction away from the supporting net frame 12. Such design will minimize the flowing resistance of the blood during it flowing out of the outflow section 1, increasing a size of the pathway for blood, and ensuring the patency of the blood flowing.

In this embodiment, the guiding bars 8 is curved with at least one inflection point. The inflection point results the guiding bar 8 expanding and shrinking alternatively in the radial direction of the outflow section 1.

Figure 6:
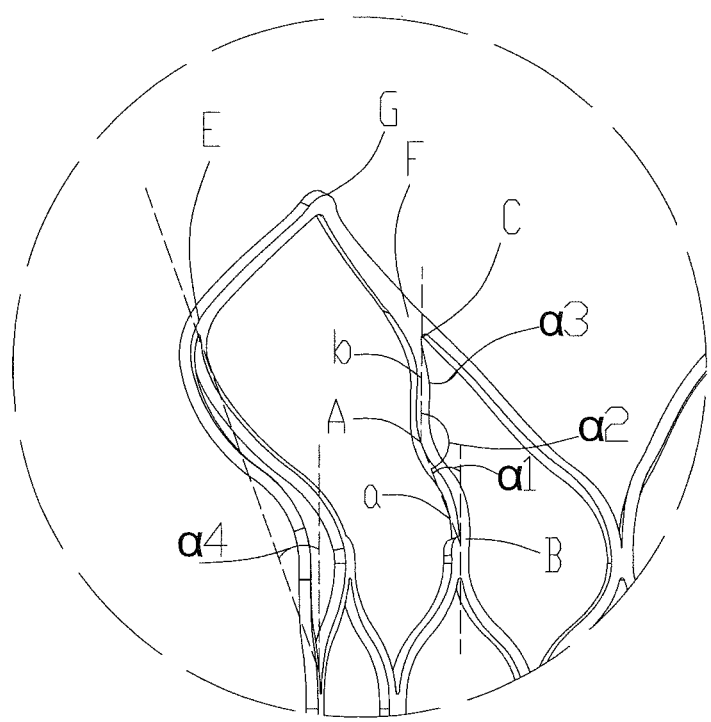
FIG. 6 is a enlarged view of the circled portion V of FIG. 5.

In particular, with referring to FIG. 6, each guiding bar is formed by two arc section. The at least one inflection point includes a first inflection point A where the two arc section intersect, and an extension direction of a first connecting line from a proximal end B of the guiding bar 8 to the first inflection point A gradually deviates from the supporting net frame 12. An extension direction of a second connecting line from the first inflection point A to a distal end C of the guiding bar 8 extends gradually towards the supporting net frame 12. Namely, the guiding bar 8 has a shape that firstly expands radially relative to an axis of the supporting net frame 12, and then shrinks radially. In addition, the shape of the guiding bar 8 may match the shape of the supporting bar 6 to facilitate to intersect the supporting bar 6. In order to match the shape of the supporting bar 6, it is improper to form a large included angle between the first connecting line and the axis of the valve stent. In the present embodiment, the included angle $\alpha_1$ between the first connecting line and the axis of the valve stent is in the range of 30° to 90°, and preferably in the range of 45° to 60°.

In this embodiment, the first connecting line connecting the proximal end B of the guiding bar 8 and the first inflection point A is the line a, and the second connecting line connecting the distal end C of the guiding bar 8 and the first inflection point A is the line b. In order to avoid the first inflection point forming a sharp corner which may pierce the sheath when the sheath is retracted, and included angle $\alpha_2$ between the first connecting line a and the second connecting line b is in the range of 90°~180°, and preferably in the range of 100°~150°.

In this embodiment, the guiding bar 8, as a whole, expands outwards relative to the axis of the valve stent, i.e., each guiding bar 8 gradually deviates away from the supporting net frame 12 from the corresponding end node 9 to the supporting bar 6. An included angle between a line connecting two ends of a respective guiding bar 8 (namely a line connecting two ends of the guiding bar along an extension direction) and an axis of the valve stent is in the range of 0° to 70°. When the included angle between the extension direction of the guiding bar 8 and the axis of the valve stent is 0°, the guiding bar has a shortest length. However, as the guiding bar 8 and the supporting bar 6 both have curved shape, and thus the guiding bar 8 will not be arranged with an extension direction thereof parallel to the axis of the supporting net frame. In addition, the guiding bar 8 needs to connected to the supporting bar 6, in order to match the shape of the supporting bar 6, it is improper to form a large included angle between the extension direction of the guiding bar 8 and the axis of the valve stent. Preferably, the line connecting two ends of a respective guiding bar 8 (i.e., a line connecting two ends of the guiding bar along an extension direction thereof) and the axis of the valve stent is in the range of 20° to 60°, more preferably in the range of 30° to 45°, and is most preferably 30°.

In this embodiment, the guiding bar 8 and a corresponding supporting bar 6 intersect at an acute angle $\alpha_3$, which is in the range of 10° to 60°, to ensure an intersection point of the guiding bar 8 and the corresponding supporting bar 6 is located at a middle portion of the outflow section 1 in the axial direction, such that the outflow section 1 has an appropriate mechanical property which is beneficial for the outflow section to expand and/or retract.

Each supporting bar 6 includes two first bar bodies 601 and a second bar body 602 connecting the distal ends of the two first bar bodies 601. The proximal end of each first bar body 601 is connected to a corresponding end node 9. The first bar body 601 deviates gradually away from the supporting net frame 12 along an extension direction from the corresponding end node 6 to the second bar body 602. The second bar body gradually extends towards the supporting net frame 12 from the intersection point with the first bar body 601, which makes the supporting bar 6 as a whole has a shape which firstly expands along a direction away from the axis of supporting net frame, and then shrinks towards the axis of the supporting net frame. As a result, the outflow section is flared shaped, and the opening at the distal end of the outflow section has an appropriate size to facilitate the retracting of the outflow section 1. In the present embodiment, each guiding bar 8 is connected to the distal end of a corresponding first bar body 601.

An included angle $\alpha_4$ between a line connecting two ends of each first bar body 601 and the axis of the supporting net frame 12 is in the range of 30° to 60°, such that the proximal end of the flared outflow section 1 has an appropriate diameter to allow blood flowing out smoothly.

In this embodiment, an obtuse angle is formed between the each first bar body 601 and the second bar body 602, as a result, the extension direction of the second bar body 602 converges towards the axis of the supporting net frame.

In this embodiment, the second bar body 602 is formed by two arc portions intersecting smoothly, and forming a sharp corner (which may be V shaped) at the intersection, this is beneficial to retract the valve stent.

Based on above descriptions, it is understood that, the flared portion of the present invention includes two segments, i.e., the inner flared segment and the outer flared segment. The outer flared segment is connected with all the end nodes of the supporting net frame 12 at the corresponding side by the inner flared segment.

Specifically, the inner flared segment gradually deviates away from the supporting net frame 12 along an extension direction from the corresponding end node 9 towards the outer flared segment. The outer flared segment gradually extends towards the supporting net frame 12 from the inner flared segment. As such, an obtuse angle is formed between the inner flared segment and the outer flared segment, which avoids sharp corn appear at the junction of the inner flared segment and the outer flared segment. In addition, the flared portion firstly expands radially, and then shrinks radially, which makes the distal end of the flared portion has an appropriate diameter to facilitate retracting of the flared portion.

The outer flared segment includes a plurality of outer flared segment units. The inner flared segment includes a plurality of inner flared segment units. Each of the outer flared segment units and the inner flared segment units includes two proximal ends and a distal end. The two proximal ends of each inner flared segment unit are connected to two corresponding end nodes 9. Each pair of two adjacent inner flared segment units corresponds to an outer flared segment unit. Two distal ends of the inner flared segment units of a pair are connected to two proximal ends of a corresponding outer flared segment unit. In this embodiment, the end nodes connected to one of the inner flared segment units of a pair are different from the end nodes connected to the other of the inner flared segment units of the pair. Two adjacent pair of inner flared segment units share a common end node 9.

In this embodiment, each outer flared segment unit is formed by a curved first strut, and each inner flared segment unit is formed by two curved second struts intersecting each other smoothly with a sharp corner formed at the intersection, so as to facilitate compressing the inner flared segment units when the flared portion is retracted. The curved first struts is formed by two arc portion intersecting each other smoothly with an sharp corner formed at the intersection, so as to facilitate compressing the outer flared segment units when the flared portion is retracted.

Each outer flared segment unit and each inner flared segment unit are both inverted V shaped.

It should be noted that, the first strut is the above described second bar body 602, the two second struts are respectively the first bar body 601 and a corresponding guiding bar 8. In addition, among each pair of inner flared segment units, the two second struts located at the inner side are defined as inner struts, and the inner struts are guiding bars 8. Among each pair of inner flared segment units, the two second struts located at an outer side are defined as outer struts, and the outer struts are the first bar bodies 601.

It is understood that, in the embodiment, the first strut extends from two distal ends of two corresponding outer struts, radially towards the supporting net frame along an extension direction of the first strut.

It should be further noted that, the first strut and the outer strut, the extension direction of the outer strut, the extension direction of the inner strut, the structure of the inner strut and the angle formed between the outer strut and the inner strut, are all the same as that described above, and will not go into detail herein.

Embodiment II

Figure 7:
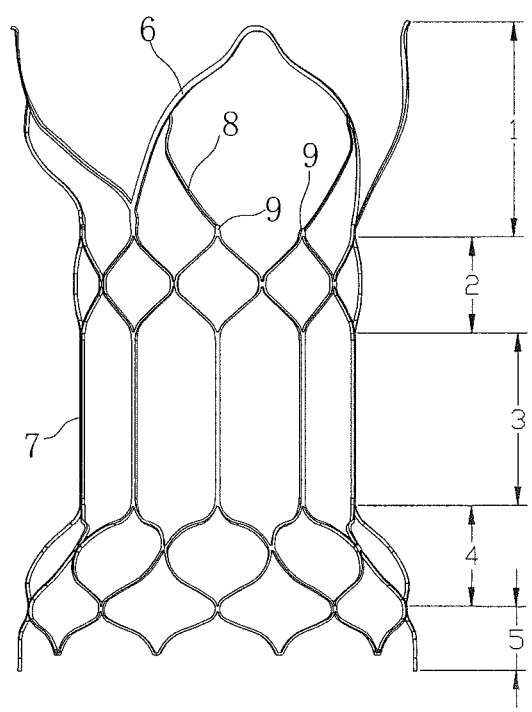
FIG. 7 is a structural schematic view of a valve stent used safely according to a second embodiment of the present invention (wherein the back side thereof is omitted).

As shown in FIG. 7, the present invention provides another pulmonary artery stent which can be used safely, including a supporting net frame, an inflow portion 5 and an outflow portion 1 connected to two axial ends of the supporting net frame respectively. A portion of the supporting net frame is a transition section 3.

a ratio of an axial length of the transition section before being compressed to an axial length of the transition section after being compressed is 1, that is, the length of the transition section 3 remains unchanged before and after being compressed, compared with the rbombic grids generally used in the prior art, the change of the axial length of the supporting net frame in the embodiment before and after being compressed can be reduced. Only if a ratio of the axial length of the transition section to the total length of the supporting net frame reaches 40% or more, the effect of the transition section can appear, that is, due to the transition section, a length of a compressed supporting net frame can be reduced so as to meet the requirement of adaptability for bending, such that the supporting net frame can easily reach a desired site inside a human body, thereby ensuring that an operation is preformed favorably.

It should noted that, although the transition section can reduce the change of the axial length of the supporting net frame before and after being compressed, it is not true that the longer the transition section the better. The reason is that, although the axial lengths of the rhombic grids generate great changes before and after being compressed, the structures of the rhombic grids contribute to the strength of the supporting net frame, and resists the impact of blood flows for a long time, and the structures of the rhombic grids enable the supporting net frame to be compressed and positioned inside the sheath pipe. Therefore, preferably, the axial length of the transition section equals 40%-90% of the total length of the supporting net frame. Further preferably, the axial length of the transition section equals 50%-80% of the total length of the supporting net frame.

In particular, the middle portion of the supporting net frame 12 is the transition section 3.

One end of the transition section 3 is connected with the inflow portion 5 via a first grid portion 4, and the other end of the transition section 3 is connected with the outflow portion 1 via a second grid portion 2. Both the first grid portion 4 and the second grid portion 2 are formed by continuous rhombic structures. Compared with the transition section 3, the first grid portion 4 expands radially to form a flared section. Rims of each rhombic structure are not exact straight lines but curved outwards slightly, and the number of the rhombic structures of the first grid portion 4 equals the number of the rhombic structures of the second grid portion 2.

The transition section 3 is formed by a plurality of straight rods 7 extending along an axial direction of the valve stent. The straight rods 7 are evenly distributed along a circumference of the valve stent, and an axial length of the transition section is about 45% of a total length of the supporting net frame.

Ends of each straight rod 7 of the transition section 3 are connected with a corresponding rhombic vertice of a rhombic unit, which faces, i.e., located adjacent to, the transition section 3. It can be seen from FIG. 7 that the straight rods 7 of the transition section 3 and the rims of the adjacent rhombic units cooperatively form hexagons, and interior angles of the hexagons are all obtuse angles.

The present invention adopts a design structure of a self-expandable valve stent, which realizes the retraction of the valve stent by the deformation of the rhombic grid section, such that the valve stent can be compressed into a sheath. Moreover, the valve stent can generate a uniform radial supporting force after being implanted into a human body, and thus the valve can be prevented from moving and dropping. As the isolated end nodes are connected to the supporting bars by the guiding bars, the risk that the end nodes pierce the sheath be eliminated, without changing adaptability of the flared section to the blood vessel.

Furthermore, the embodiment II of the present invention can reduce almost 50% of the amount of metal material used by the valve stent (which is usually memory alloy, the present invention uses nickel-titanium alloy), not only reduces a diameter of the valve stent after being compressed, but also improves the adaptability for bending, so that the passing-through performance of the valve in the blood vessel is further enhanced.

The present invention further provides a valve replacement device, which includes an aforementioned valve stent and a prosthesis valve fixed inside the supporting net frame. When the valve stent reaches a predetermined site inside a human body via a transport system, the valve stent is released from a sheath and then expands, and the prosthesis valve fixed inside the valve stent replaces the natural valve of the human body to realize the function of enabling blood to pass unidirectionally.

The features of the embodiments described above can be combined arbitrarily, and in order to make the description simple, all possible combinations of the respective features in the above embodiments are not described. However, as long as there is no conflict in the combination of these features, the combination should be considered to be within the scope of the specification.

The embodiments described above are merely illustrative of several embodiments of the invention and are described more specifically and detailed, but are not meaning to limit the scope of the invention. It should be noted that various modifications and improvements can be made by those skilled in the art without departing from the spirit of the invention, which are also included within the scope of the present invention. Accordingly, the scope of the present invention should be determined based on the claims.

What is claimed is:

1. A valve stent, comprising:
   a supporting net frame having a plurality of grids, with each grid defined by a plurality of struts connected together at nodes, the supporting net frame having opposing first and second frame ends, and with the nodes at each frame end being defined as end nodes; and
   a flared section connected to the first frame end of the supporting net frame, wherein the flared section comprises a plurality of supporting bars and a plurality of guiding bars:
   wherein each supporting bar has a first supporting bar end and the first supporting bar ends of two adjacent supporting bars are connected to one of the end nodes;
   wherein each guiding bar has opposing first and second guiding bar ends, with each first guiding bar end connected to a first one of the end nodes adjacent to a second one of the end nodes where two first supporting bar ends are connected, and each second guiding bar end is connected to a part of the adjacent supporting bar at a location spaced apart from the first supporting bar end;
   wherein each supporting bar has a second supporting bar end that is connected to a second supporting bar end of another one of the plurality of supporting bars, and
   wherein the another one of the plurality of supporting bars is different from the supporting bar to which the supporting bar's first supporting bar end shares an end node.

2. The valve stent of claim 1, wherein the plurality of supporting bars are curved, and the plurality of curved supporting bars defines an outer rim of the flared section.

3. The valve stent of claim 1, wherein each end node is directly connected to one of the plurality of supporting bars or indirectly connected to one of the plurality of supporting bars via one of the plurality of guiding bars.

4. The valve stent of claim 1, wherein each of the plurality of guiding bars is curved and has at least one inflection point.

5. The valve stent of claim 4, wherein each guiding bar is formed by two arc sections and the at least one inflection point comprises a first inflection point.

6. The valve stent of claim 5, wherein the supporting net frame has a central axis, each guiding bar has an extension direction from the first guiding bar end through the first inflection point to the second guiding bar end, and wherein for each guiding bar, there is a first connecting line between the first guiding bar end and where the guiding bar meets the first inflection point that gradually deviates away from the central axis of the supporting net frame along the extension direction.

7. The valve stent of claim 6, wherein an included angle of the first connecting line of each guiding bar and the central axis of the supporting net frame ranges from 30 degrees to 90 degrees.

8. The valve stent of claim 6, wherein an included angle of the first connecting line of each guiding bar and the central axis of the supporting net frame ranges from 45 degrees to 60 degrees.

9. The valve stent of claim 6, wherein for each guiding bar, there is a second connecting line between the second guiding bar end and where the guiding bar meets the first inflection point that extends gradually towards the central axis of the supporting net frame along the extension direction.

10. The valve stent of claim 9, wherein an included angle of the first connecting line and the second connecting line ranges from 90 degrees to 180 degrees.

11. The valve stent of claim 9, wherein an included angle of the first connecting line and the second connecting line ranges from 100 degrees to 150 degrees.

12. The valve stent of claim 1, wherein a first acute angle is formed between each guiding bar and a respective one of the plurality of supporting bars.

13. The valve stent of claim 12, wherein the first acute angle ranges from 10 degrees to 60 degrees.

14. The valve stent of claim 1, wherein the supporting net frame has a central axis, each supporting bar has a second inflection point and has an extension direction from its first supporting bar end through the second inflection point to its second supporting bar end, and wherein each of the supporting bars first deviates gradually away from the central axis of the supporting net frame along the extension direction from the first supporting bar end to the second inflection point, and then extends towards the central axis of the supporting net frame from the second inflection point to the second supporting bar end.

15. The valve stent of claim 14, wherein for each supporting bar, there is a line between the first supporting bar end and the second inflection point, and an included angle between the line and the central axis of the supporting net frame ranges from 30 degrees to 60 degrees.

16. The valve stent of claim 1, wherein the supporting net frame comprises a blood inlet for allowing blood to flow in, and a blood outlet opposite to the blood inlet, and the blood outlet is the first frame end of the supporting net frame.

17. The valve stent of claim 1, wherein the supporting net frame comprises a transition section between the first and the second frame ends, and wherein a ratio of an axial length of the transition section before being compressed to an axial length of the transition section after being compressed is 1.

18. A valve replacement device, comprising the valve stent of claim 1; and a prosthesis valve attached inside the supporting net frame.

19. The valve replacement device of claim 18, wherein the valve stent is a pulmonary valve stent.

* * * * *